United States Patent
Kwock

(10) Patent No.: US 9,775,874 B1
(45) Date of Patent: Oct. 3, 2017

(54) METHOD FOR TREATING SYMPTOMS OF HORMONE IMBALANCE

(71) Applicant: The Daily Wellness Company, Honolulu, HI (US)

(72) Inventor: Denny W. Kwock, Honolulu, HI (US)

(73) Assignee: The Daily Wellness Company, Honolulu, HI (US)

( * ) Notice: Subject to any disclaimer, the term of this patent is extended or adjusted under 35 U.S.C. 154(b) by 136 days.

(21) Appl. No.: 14/041,146

(22) Filed: Sep. 30, 2013

Related U.S. Application Data

(60) Provisional application No. 61/710,113, filed on Oct. 5, 2012, provisional application No. 61/706,887, filed on Sep. 28, 2012.

(51) Int. Cl.
| | |
|---|---|
| *A61K 36/83* | (2006.01) |
| *A61K 36/85* | (2006.01) |
| *A61K 36/53* | (2006.01) |
| *A61K 31/155* | (2006.01) |
| *A61K 31/355* | (2006.01) |
| *A61K 31/519* | (2006.01) |
| *A61K 31/675* | (2006.01) |
| *A61K 31/714* | (2006.01) |
| *A61K 33/04* | (2006.01) |
| *A61K 33/06* | (2006.01) |
| *A61K 33/26* | (2006.01) |
| *A61K 33/30* | (2006.01) |
| *A61K 36/82* | (2006.01) |

(52) U.S. Cl.
CPC ............ *A61K 36/53* (2013.01); *A61K 31/155* (2013.01); *A61K 31/355* (2013.01); *A61K 31/519* (2013.01); *A61K 31/675* (2013.01); *A61K 31/714* (2013.01); *A61K 33/04* (2013.01); *A61K 33/06* (2013.01); *A61K 33/26* (2013.01); *A61K 33/30* (2013.01); *A61K 36/82* (2013.01); *A61K 36/83* (2013.01); *A61K 36/85* (2013.01)

(58) Field of Classification Search
None
See application file for complete search history.

(56) References Cited

U.S. PATENT DOCUMENTS

| | | | |
|---|---|---|---|
| 6,497,885 B2 | 12/2002 | Trant | |
| 6,610,331 B1 * | 8/2003 | Sweazy et al. | 424/757 |
| 2002/0192310 A1 * | 12/2002 | Bland | A23L 33/105 424/745 |
| 2008/0038367 A1 * | 2/2008 | Saloum | 424/617 |

OTHER PUBLICATIONS

Weisskopf et al. (Planta Med 2005; 71:910-916).*
Hendra et al. (BMC Complementary and Alternative Medicine 2011, 11:110).*
Faried et al. (International Journal of Oncology 2007, 30(3), abstract).*
Dawood, M. Yusoff; American Journal of Obstetrics and Gynecology; vol. 169, issue 5; Nov. 1993; abstract.*

* cited by examiner

*Primary Examiner* — Abigail Fisher
*Assistant Examiner* — Jessica Kassa
(74) *Attorney, Agent, or Firm* — James Creighton Wray; Meera P. Narasimhan

(57) ABSTRACT

In a new supplemental combination and method of treatment, the herbs Vitex agnus-castus (chasteberry), green tea, and arginine treat premenstrual syndrome, premenstrual tension, as an alternative to conventional women's hormone replacement therapy, and to offset the problems related to sub-optimal hormone balance or decline resulting from age, genetics, stress, or environmental influences. Furthermore, the combination may be enhanced with a phytoestrogen and/or a progesterone-receptor enhancing agent.

4 Claims, No Drawings

METHOD FOR TREATING SYMPTOMS OF HORMONE IMBALANCE

This application claims the benefit of U.S. Provisional Application No. 61/710,113, filed Oct. 5, 2012, and U.S. Provisional Application No. 61/706,887, filed Sep. 28, 2012, which are hereby incorporated by reference in their entirety as if fully set forth herein.

SUMMARY OF THE INVENTION

Delayed sub-optimal hormone imbalance in post-menopausal women results from age, genetics, stress, environmental influences, child bearing, unhealthy diets and use of tobacco, caffeine, alcohol, drugs and contaminants.

Need exists for pharmaceutical compounds and treatment methods that improve symptoms of premenstrual syndrome and premenstrual tension.

The use of the present invention treats symptoms of hormone imbalances as an alternative to conventional women's hormone replacement therapy. Using the hormone imbalance supplements of the present invention also is useful in reducing premenstrual syndrome and premenstrual tension.

The present invention provides combinations of bioeffecting compounds and methods for treating symptoms of hormone imbalance. The combinations and methods include nutritional components that benefit premenstrual syndrome and premenstrual tension. All components have been studied separately to determine their individual efficacy. The invention provides the first products and methods to put these components together synergistically in women's formulations.

The present invention is drawn to a gentle, natural formula that has been clinically shown to help a woman's body achieve its own unique Youthful Hormone Balance compensating for the effects of age, stress, poor diet, and environmental toxins.

Benefits of the present invention include improved mood, more energy, better sleep, more comfortable and regular menstrual cycles, less weight gain around the hip and waist areas, and healthier skin and hair. The formula and method of treatment of the present invention is generally for women with premenstrual syndrome (PMS) and premenstrual tension, post menopausal symptoms, and women 35 years of age or older wanting to feel like their younger self again.

The invention is a natural formula that gently supports the body's own optimal hormone balance while containing no hormones.

In many of these cases, the causes of premenstrual syndrome and premenstrual tension are treatable. Nutritional and lifestyle changes should be the first step in treating premenstrual syndrome and premenstrual tension. Smoking and caffeine, drug and alcohol consumption, environmental toxicants, and stress are related to premenstrual syndrome and premenstrual tension in women. Reproductive organs are highly susceptible to free radical or oxidative damage from environmental toxicants and natural aging. A balanced, nutritional diet, and nutritional supplements with high antioxidant content can help treat some of these symptoms. In women, hormone balance is critical to monthly ovulation and development of the corpus leteum (an ovarian follicle that release progesterone after release of the egg to prepare the uterus for implantation). Hormone balance is and has been recognized as important in post-menopausal women. Estrogen has been used for lost hormone replacement in hormone replacement therapy (HRT). However, discovery of estrogen responsive ER-positive cancers has reduced use of estrogen HRT.

The invention provides a solution to the problem of keeping hormone balances for youthful energy and appearance without the dangers of estrogen HRT.

These and other objects and features of the invention are apparent in the disclosure, which includes the above ongoing written specification with the claims.

DETAILED DESCRIPTION OF THE PREFERRED EMBODIMENTS

The invention provides combinations of beneficial bioeffecting compounds for maintaining and restoring hormone balance in post-menopausal women, and reducing premenstrual syndrome and premenstrual tension in women. The invention provides a scientifically validated herbal/nutritional blend for women to improve and treat symptoms of premenstrual syndrome and premenstrual tension by helping to regulate the menstrual cycle and correct hormone imbalance (corpus luteum insufficiency). The combination of amino acids, herbs, vitamins and minerals improves overall health and helps with many of the deficiencies that accompany symptoms of premenstrual syndrome and premenstrual tension.

The herb, Vitex agnus-castus (chasteberry), enhances hormone balance by increasing progesterone release and, therefore, ovulation frequency. The antioxidants, green tea, vitamin E, and selenium, improve overall reproductive health. L-arginine, an amino acid, stimulates the reproductive, endocrine, and other hormone-producing organs by improving circulation. Folic acid, vitamins B6 and B12, iron, zinc and magnesium help promote womens' overall health necessary for optimal hormone balance.

The invention provides combinations of beneficial bioeffecting compounds for symptoms of premenstrual syndrome and premenstrual tension in women. Vitamins C and E, coenzyme Q10 and selenium are all potent antioxidants that help create a healthier physiology that promotes a more optimal hormone balance. Ferulic acid, an antioxidant found in Dong quai, zinc and B vitamins (B6, B12 and folate) are nutrients also beneficial in this way.

A method for treating symptoms of premenstrual syndrome or premenstrual tension is disclosed. The method comprises ingesting an ingestible dietary supplement having ingredients of vitex agnus and arginine, and taking the ingestible dietary supplement as an alternative to conventional hormone replacement therapy and offsetting problems of sub-optimal hormone balance or decline resulting from age, genetics, stress, or environmental influences.

A method for treating symptoms of premenstrual syndrome or premenstrual tension is disclosed. The method comprises ingesting an ingestible dietary supplement having ingredients of vitex agnus and green tea, and taking the ingestible dietary supplement as an alternative to conventional hormone replacement therapy and offsetting problems of sub-optimal hormone balance or decline resulting from age, genetics, stress, or environmental influences.

The present invention is also drawn to counteract "endocrine disrupters," especially external agents and environmental contaminants that have an estrogenic effect called "xenoestrogens."

In another embodiment, a "phytoestrogen" is added to the formulation. This might include, but is not limited to, soy, black cohosh, or wild yam extract. A phytoestrogen competitively binds estrogen receptors in the body to prevent stronger estrogens like xenoestrogens from having a more biologically potent estrogenic effect. In effect, this better improves the progesterone-enhancing ability of the base formula to overcome estrogen dominance that can cause the problematic symptoms listed in this patent application.

In a further embodiment, a "progesterone-receptor" enhancing ingredient is added to the formulation. This improves the progesterone to estrogen balance in women's body to overcome estrogen dominance. Such an ingredient is phaleria macrocarpa, a botanical ingredient reported to increase progesterone receptors.

The invention provides synergistic action of the combinations.

The two dietary supplements in female formulas are useful for women. Preferably, the distinct combinations are taken by females between the ages is between 21 and older, preferably 35+ years of age. The distinct combinations are useful for women who have sought relief from symptoms associated with premenstrual syndrome and premenstrual tension without success. Preferably, patients take 2-4 capsules per day of the distinct formulas for three months.

Table 1 shows the preferred ranges of the combinations considered in percent by weight.

TABLE 3

| Hormone Balance Formula: | mg/dose | % DV | % by wt. | mg/3 caps | mg/cap | |
|---|---|---|---|---|---|---|
| L-arginine base | 800 | | 47.92% | 800.00 | 266.67 | 98-99% purity |
| Magnesium (oxide)-60% | 400 | 100 | 23.96% | 666.67 | 222.22 | |
| Green tea-50% polyphenols | 200 | | 11.98% | 220.00 | 73.33 | |
| Iron (gluconate)-11% | 18 | 100 | 1.08% | 163.64 | 54.55 | |
| Vitamin E-alpha tocopherol-1.185 mg/iu | 150 | 500 | 8.98% | 140.00 | 46.67 | |
| Zinc (gluconate)-13% | 15 | 100 | 0.90% | 115.38 | 38.46 | |
| Vitex agnus-castus 0.5% | 80 | | 4.79% | 40.00 | 13.33 | special order from Germany |
| Selenium TCP-0.2% | 0.07 | 100 | 0.00% | 35.00 | 11.67 | |
| Vitamin B6-82% | 6.0 | 300 | 0.36% | 7.20 | 2.40 | |
| Vitamin B12 (1%) | 0.012 | 200 | 0.00% | 1.44 | 0.48 | |
| Folic acid | 0.4 | 100 | 0.02% | 0.48 | 0.16 | |
| Rice flour* | | | | 284.70 | 94.90 | |
| Mg stearate* | | | | 78.00 | 26.00 | |
| Silica* | | | | 0.00 | 0.00 | |
| | 1669.48 | | 100.00% | 2552.51 | 850.84 | |

Acceptable ranges or womens' formulations are shown in Tables 2 and 3.

TABLE 2

| Components | Minimum % | Maximum % |
|---|---|---|
| Vitex (chasteberry) | 2 | 10 |
| L-arginine | 40 | 60 |
| Green tea | 5 | 20 |
| Vitamin E | 5 | 20 |
| Selenium | 0.01 | 1 |
| Vitamins B6, B12 | 0.01 | 1 |
| Folic acid | 0.01 | 1 |
| Iron | 0.1 | 5 |
| Magnesium | 10 | 40 |
| Zinc | 0.001 | 1 |

TABLE 3

| Components | Minimum % | Maximum % |
|---|---|---|
| Vitex (chasteberry) | 1 | 20 |
| L-arginine | 20 | 70 |
| Green tea | 0 | 30 |
| Vitamin E | 0.01 | 30 |
| Selenium | 0 | 2 |
| Vitamins B6, B12 | 0 | 2 |
| Folic acid | 0 | 2 |
| Iron | 0 | 7 |
| Magnesium | 0 | 50 |
| Zinc | 0 | 10 |

Examples of useful formulation in percent by weight are shown in Table 4.

TABLE 4

| Components | Wt % |
|---|---|
| Vitex (chasteberry) | 5 |
| L-arginine | 50 |
| Green tea | 11 |

TABLE 4-continued

| Components | Wt % |
|---|---|
| Vitamin E | 11 |
| Selenium | 0.1 |
| Vitamins B6, B12 | 0.38 |
| Folic acid | 0.02 |
| Iron | 1 |
| Magnesium | 20 |
| Zinc | 1 |

While the invention has been described with reference to specific embodiments, modifications and variations of the invention may be constructed without departing from the scope of the invention.

I claim:

1. A pharmaceutical composition consisting of an ingestible dietary supplement for treating symptoms of hormone imbalance, hormonal decline, premenstrual tension, or premenstrual syndrome in females, the ingestible dietary supplement consisting of in combination components in effective amounts of Vitex agnus-castus (chasteberry), antioxidants, L-arginine, a phytoestrogen, a progesterone-receptor enhancer Phaleria macrocarpa, folic acid, vitamin B6, vitamin B12, iron, zinc, and magnesium; wherein the antioxidants are selected from the group consisting of green tea, vitamin E, selenium, and combinations thereof, the ingestible dietary supplement of the pharmaceutical composition taken as an alternative to conventional hormone replacement therapy to offset problems of sub-optimal hormone balance or decline resulting from age, genetics, stress, or environmental influences, wherein the components are present in the proportion in parts by weight of about 2 to 20% Vitex agnus-castus (chasteberry), about 5 to 50% antioxidants selected from the group consisting of green tea, vitamin E, selenium, and combinations thereof, about 10 to 80% L-arginine, about 0.001 to 1% folic acid, about 0.001 to 1% vitamin B6 and vitamin B12, about 0.1 to 10% iron, about 0.1 to 10% zinc, and about 5 to 50% magnesium.

2. The pharmaceutical composition of claim 1, wherein the phytoestrogen is selected from the group consisting of soy, black cohosh, and wild yam extract.

3. A method for treating symptoms of premenstrual syndrome or premenstrual tension, the method comprising ingesting the pharmaceutical composition of claim 1.

4. A method for treating symptoms of premenstrual syndrome or premenstrual tension, the method comprising ingesting the pharmaceutical composition of claim 2.

* * * * *